United States Patent [19]
Huang et al.

[11] Patent Number: 4,929,788
[45] Date of Patent: May 29, 1990

[54] PROCESS FOR SEPARATING 1-DODECENE AND 1-TETRADECENE FROM AN ALUMINUM ALKYL CHAIN GROWTH PRODUCT

[75] Inventors: C. S. Warren Huang, Chesterfield, Mo.; Karl W. Meyer, Webster, Tex.

[73] Assignee: Ethyl Corporation, Richmond, Va.

[21] Appl. No.: 345,699

[22] Filed: May 1, 1989

[51] Int. Cl.$^5$ .............................. B01D 3/00; C07C 7/04
[52] U.S. Cl. ...................................... 585/522; 203/80; 203/88; 203/91; 585/511
[58] Field of Search ........................ 203/88, 91, 73, 80; 585/522, 511

[56] References Cited

U.S. PATENT DOCUMENTS

| | | | |
|---|---|---|---|
| 3,218,343 | 11/1965 | Acciarri et al. | 585/328 |
| 3,227,773 | 1/1966 | Roming, Jr. | 585/328 |
| 3,249,648 | 5/1966 | Carter et al. | 585/328 |
| 3,412,126 | 11/1968 | Gautreaux | 585/328 |
| 3,751,518 | 8/1973 | Hagan et al. | 585/328 |
| 3,789,081 | 1/1974 | Lanier | 585/328 |
| 3,906,053 | 9/1975 | Lanier | 203/39 |
| 4,435,606 | 3/1984 | Motz et al. | 585/328 |

FOREIGN PATENT DOCUMENTS

| | | | |
|---|---|---|---|
| 0725225 | 1/1966 | Canada | 585/328 |
| 1920726 | 11/1970 | Fed. Rep. of Germany | 585/328 |
| 50-17442 | 6/1975 | Japan . | |
| 1070837 | 6/1967 | United Kingdom | 585/328 |

OTHER PUBLICATIONS

Arnold Weissberger, "Technique of Organic Chemistry", Distillation, vol. IV, p. 3.

Primary Examiner—Virginia Manoharan
Attorney, Agent, or Firm—Joseph D. Odenweller

[57] ABSTRACT

Dodecene-1 and 1-tetradecene can be rectified from a mixture containing 1-dodecene and 1-tetradecene and triethylaluminum ("TEA") which has about the same normal boiling point as 1-dodecene and 1-tetradecene by feeding the above mixture to an intermediate point of a rectification column maintained under sufficient vacuum (e.g. 5–30 torr) such that the temperature at the intermediate feed point is about 250°–260° F. and the overhead distillation temperature is about 190°–240° F. The TEA which normally boils at about the same temperature as 1-dodecene and 1-tetradecene will exist as a dimer permitting part of the 1-dodecene and 1-tetradecene to distill overhead and most of the TEA to exit the bottom of the column.

8 Claims, 1 Drawing Sheet

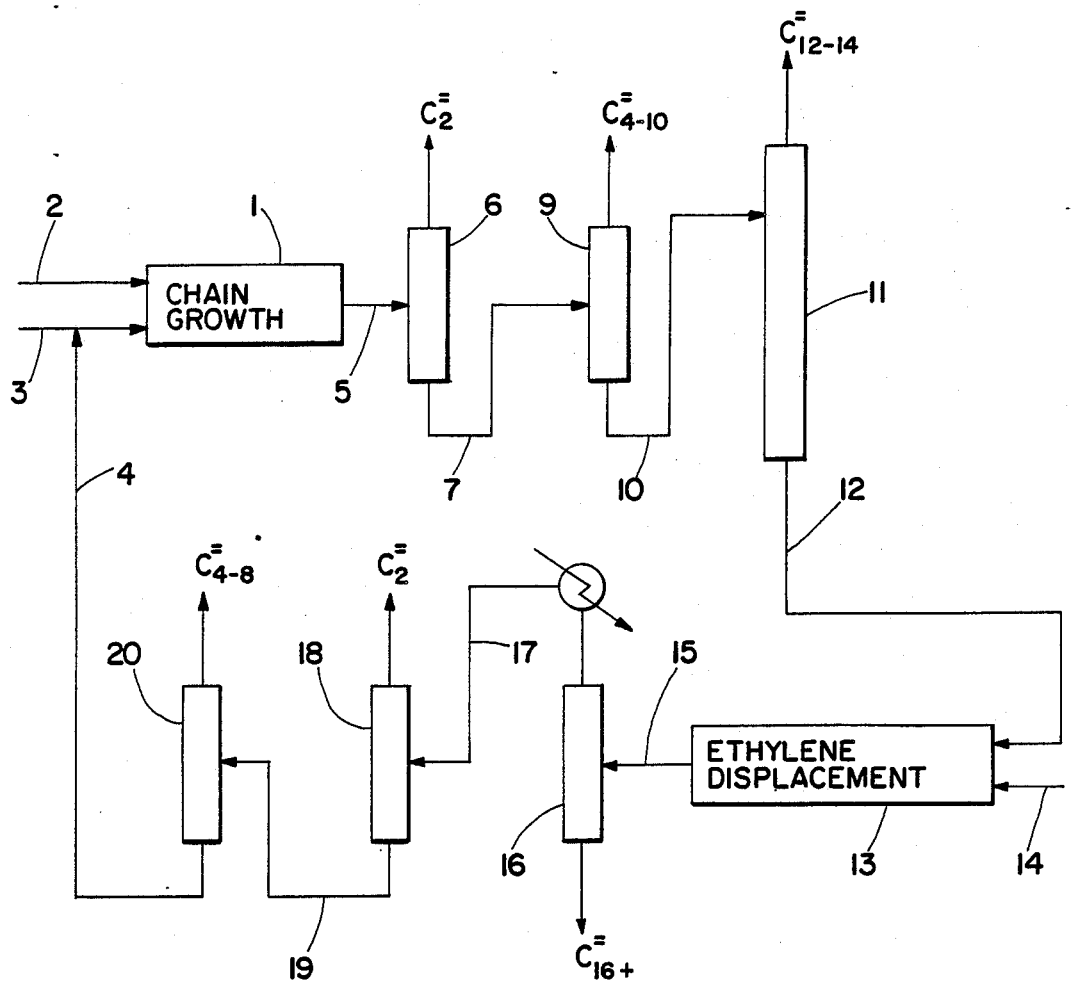

PROCESS FOR SEPARATING 1-DODECENE AND 1-TETRADECENE FROM AN ALUMINUM ALKYL CHAIN GROWTH PRODUCT

BACKGROUND

Alpha-olefins are made in commercial quantities by a process developed in the fifties by Karl Ziegler and his coworkers. The so-called Ziegler process involves the reaction of triethyl aluminum (TEA) and ethylene at temperatures in the range of 200°–350° F. and pressure in the range of 2000–5000 psig to yield a mixture of tri-$C_{2-20+}$ alkyl aluminum having a poisson distribution and $C_{2-20}$ olefins. The ethylene is flashed from the reaction mixture for recycle and the light olefins through 1-decene can be distilled from the mixed aluminum alkyls since they have a normal boiling point below the lightest aluminum alkyl (viz. TEA). In the past, attempts to distill 1-dodecene and 1-tetradecene from the mixed aluminum alkyls resulted in a substantial amount of the TEA and other light aluminum alkyls co-distilling with the 1-dodecene and 1-tetradecene. This light aluminum alkyl represents an economic penalty because it must be hydrolyzed which also serves to contaminate the α-olefin product with paraffins, e.g. ethane, butane and hexane.

This problem was recognized in Roming et al. U.S. Pat. No. 3,227,773 wherein the patentees state:

"Some prior art processes have been limited generally to the production of $C_{8-10}$ olefins, since no practical methods were known for completely separating olefins boiling close to $C_{10-14}$ olefins from the $C_2$ or $C_3$ alkyl aluminum remaining after the displacement reaction. Thus, the $C_{12}$ and higher olefins could not be economically distilled overhead from the liquid alkyl aluminum due to the relatively low decomposition temperature of said alkyl aluminum and/or the closely similar boiling ranges of lower alkyl aluminum and these higher olefins."

From this it is apparent that a need exists for an efficient method of separating $C_{12-14}$ α-olefins from aluminum alkyls containing light alkyls such as TEA. It is an object of the present invention to provide such a method.

SUMMARY

According to the present invention, $C_{12-14}$ α-olefins can be distilled from a mixture of olefins and aluminum alkyls containing $C_{12-14}$ α-olefins and triethyl aluminum by conducting the distillation in a rectification column under sufficient vacuum to maintain the rectification section of the column at a temperature in the range of about 200°–250° F.

BRIEF DESCRIPTION OF THE DRAWING

The drawing is a schematic flow diagram of an α-olefin process using aluminum alkyl chain growth and displacement and including a rectification column for distilling $C_{12-14}$ α-olefins from a mixture containing $C_{12-14}$ α-olefins and triethyl aluminum.

In the drawing an olefin is represented by "C=" and a subscript integer which specifies the number of carbon atoms in the olefin. Thus $C_2=$ is ethylene, $C_4=$ is butene, $C_{4-10}=$ represents olefin from butene to decene and $C_{16+}=$ represents olefins containing 16 or more carbon atoms. Most of the olefins are linear α-olefins although minor amounts of internal and branched olefins may be present.

DESCRIPTION OF THE PREFERRED EMBODIMENTS

A preferred embodiment of the invention is a process for separating an aluminum alkyl chain growth product comprising $C_{12-14}$ α-olefins and triethyl aluminum said process comprising:

(A) feeding said chain growth product to an intermediate point of a rectification column, said rectification column being maintained under vacuum such that in operation the rectification section above said intermediate point is at a temperature in the range of 200°–250° F. whereby triethyl aluminum entering said rectification section is mainly in the form of triethyl aluminum dimer thereby increasing its molecular weight and decreasing its volatility, (B) distilling at least part of said $C_{12-14}$ α-olefins overhead from said rectification section and (C) removing a major portion of said triethyl aluminum as a bottoms stream from said rectification column.

The process embodies a vacuum rectification column, either as a separate unit or as part of aluminum alkyl chain growth α-olefin process. The process separates at least part of the $C_{12-14}$ olefin, e.g. 1-dodecene and 1-tetradecene from a mixture which includes TEA, with minimal TEA contamination of the distillate and thus, little loss of TEA and minimal paraffin contamination of the α-olefin products. This has been considered impossible in the past because of the close proximity of the normal boiling points of 1-dodecene, 1-tetradecene and TEA. In fact 1-tetradecene is reported to have a normal boiling point above that of TEA, 250°–260° C. vs. 187° C. Previous attempts at such a distillation have resulted in large amounts of TEA in the $C_{12-14}$ α-olefin distillate. Removal of this triethyl aluminum by hydrolysis results in large losses of aluminum alkyl value as well as paraffin contamination of the α-olefin products placing a severe economic penalty on the process.

The present process permits the distillation of at least part of the 1-dodecene and 1-tetradecene in an olefin mixture which contains both TEA 1-dodecene and 1-tetradecene. By "at least part" is meant at least 10 weight percent and generally at least 20 weight percent of the 1-dodecene and 1-tetradecene in the mixture fed to the column. At the same time a major amount of the TEA in the feed is rejected into the column bottoms. By "a major amount" is meant over 50 weight percent. In practice, it has been possible to reject 75–95 weight percent of the TEA in the feed into the column bottoms.

The present process takes advantage of the fact that TEA exists as a dimer as long as it is maintained below a critical temperature. The dimer has the structure:

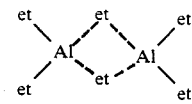

wherein "et" represents an ethyl group.

Previous attempts to distill $C_{12-14}$ α-olefins have exceeded this critical temperature causing the TEA dimer to disassociate to form TEA monomer which readily co-distills with the $C_{12-14}$ α-olefins. TEA dimer has a much lower vapor pressure and tends not to pass up through a rectification column if the column is maintained under a vacuum sufficient to cause at least part of the $C_{12-14}$ α-olefins to distill and at the same time maintain the temperature in the rectification section of the column below about 250° F., for example in the range of 200°–250° F., more preferably 220°–230° F. The precise vacuum needed to achieve these conditions may vary somewhat with the overall composition being rectified but is generally in the range of 5–30 torr, more often 15–25 torr.

The mixtures that are separated by the present process all contain at least some TEA and $C_{12-14}$ α-olefins. Other components may be present in the mixture as well. For example a typical TEA chain growth product will contain TEA as well as a poisson distribution of tri-$C_{2-20+}$ alkyl aluminum and possibly even higher alkyl aluminums. Such mixture also include ethylene which is conventionally flashed off immediately following the chain growth stage. By "flashed off" is meant passed through a vapor-liquid separator which permits the more volatile components to vaporize but does not have any substantial rectification effect.

After the ethylene is removed the ethylene-stripped chain growth product will contain any $C_{4-20+}$ olefins that might have formed in the chain growth reactor via incidental displacement as well as $C_{4-20}$ α-olefins that might have been recycled to the chain growth reactor as solvent.

A suitable feed to the rectification column might include:
5–75 weight percent aluminum alkyls of which 2–10 weight percent is TEA and the remainder higher trialkyl aluminum
25–95 weight percent α-olefins of which 5–90 weight percent are $C_{12-14}$ α-olefins.

The rectification column may be any of the several known types including those with individual trays or it may be a packed column. The preferred rectification column is a packed column using structured packing which has a very low liquid hold up. Structured packing is a series fabricated mass transfer units stacked one upon another in the column. They consist of corrugated stainless steel structures, sometimes perforated, that are bonded together in units and installed in the distillation column. One such unit is Flexipac ® structured packing manufactured by Koch Engineering Co., Houston, Tex.

The rectification section of the column is the section above the intermediate point where the mixture to be separated is introduced. The rectification section should have at least one theoretical stage. There is no real maximum number of stages in the rectification section but little is gained by exceeding three stages. Excellent results have been achieved using a rectification column having one theoretical stage in the rectification section and four stages below the rectification section.

Tests were carried out to demonstrate the feasability of distilling $C_{12-14}$ α-olefins from a mixture containing TEA and $C_{12-14}$ α-olefins. The tests utilized a column 2 inch diameter with 13 actual trays. The column was an Oldershaw column with sieve trays. The feed point was three trays down from the top such that the rectification section above the feed point had about 1.5 theoretical trays. The column was maintained at a pressure of 19–26 torr.

The feed mixture consisted of:

| Component | Weight Percent |
|---|---|
| 1-dodecene | 12.9 |
| 1-tetradecene | 8.1 |
| 1-hexadecene | 4.3 |
| TEA | 0.635 |
| tri-$C_{4-20+}$ alkyl aluminum | 56.8 |

Feed to the column was at the rate of 1.0 ml/min. The column temperature at the feed tray was 216°–256° F. and the overhead temperature was 190°–233° F. The temperature at the bottom of the column was 320°–335° F. and the reboiler temperature was 340°–346° F.

The overhead distillate was analyzed by gas chromatography and found to consist of:

| | Weight Percent |
|---|---|
| 1-dodecene | 34.6 |
| 1-tetradecene | 12.1 |
| TEA | 0.43 |

The bottoms were analyzed and found to contain:

| | Weight Percent |
|---|---|
| 1-tetradecene | 6.4 |
| 1-hexadecene | 5.8 |
| TEA | 0.72 |
| tri-$C_{4-20+}$ alkyl aluminum | 80.4 |

This bench test demonstrated the operability of the process for distilling 1-dodecene and 1-tetradecene from a mixture which contained TEA while rejecting most of the TEA to the bottoms stream.

The use of the separation process in a typical aluminum alkyl chain growth α-olefin process can be described with reference to the drawing. In the drawing, ethylene is shown as $C_2=$, butene as $C_4=$, and so forth.

Ethylene and TEA are fed to the chain growth reactor 1 through conduits 2 and 3 respectively. Recycle aluminum alkyls including TEA plus a broad range of olefins are also fed to reactor 1 through recycle conduit 4. A stoichiometric excess of ethylene is used. A useful ethylene/TEA mole ratio is about 4–10/1. Chain growth reactor 1 is maintained under chain growth conditions, typically 200°–300° F. at 2000–3500 psig for a 20–60 minute residence time.

Growth product is transferred via conduit 5 to flash separator 6 operating at a lower pressure, e.g. 400–700 psig, causing ethylene to vaporize. This ethylene is pumped back to chain growth reactor 1 as part of the ethylene feed.

The liquid phase from flash unit 6 comprises residual ethylene, $C_{4-20+}$ α-olefins, TEA and poisson tri-$C_{4-20+}$ alkyl aluminums. This liquid is transferred via conduit 7 to flash distillation unit 9 wherein a further pressure drop causes vaporization of $C_{4-10}$ α-olefins. Optionally flash distillation unit 9 can be a series of two or more separate flash distillation units each sequentially at a lower pressure to remove $C_{4-10}$ α-olefins in stages. In either case, the residual liquid phase from unit 9 comprises $C_{12-20+}$ α-olefins, TEA and a poisson distribution mixture of tri-$C_{4-20+}$ alkyl aluminums. This liquid is fed via conduit 10 to an intermediate point in rectification column 11. Rectification column 11 is packed with low hold-up fabricated stainless steel structured packing to give the equivalent of one theoretical tray above the intermediate feed point and 4 trays below the feed point. The pressure in rectification column 11 is reduced to about 15-20 torr causing $C_{12-14}$ α-olefins to be rectified overhead. The rectification section temperatures range from about 250°-260° F. at the intermediate feed point to about 190°-240° F. overhead.

The bottoms stream from column 11 comprises $C_{14-20+}$ α-olefins, TEA and the poisson distribution tri-$C_{4-20+}$ alkyl aluminum. This bottom stream is conveyed via conduit 12 to ethylene displacement reactor 13. Ethylene is also fed via conduit 14 to displacement reactor 13 at a stoichiometric excess over that required to displace all alkyls in the tri-$C_{4-20+}$ alkyl aluminum. Ethylene feed of 5-10 moles per mole of tri-$C_{4-20+}$ alkyl aluminum in the feed has been found to be satisfactory.

Displacement reactor 13 is maintained under displacement conditions of about 450°-700° F. and 200-500 psig. Displacement is rapid and residence times of 0.1-2 seconds are adequate.

Effluent from displacement reactor 13 comprises ethylene, $C_{4-20+}$ α-olefins, TEA and minor amounts of higher alkyl aluminums. This effluent is transferred via conduit 15 to distillation unit 16 which removes mainly TEA and $C_{2-14}$ olefins overhead. The bottoms from unit 16 comprise mainly $C_{16+}$ olefins and some residual higher alkyl aluminums. This can be recovered by air oxidation and hydrolysis followed by distillation to recover $C_{16+}$ α-olefins and optionally $C_{16+}$ alcohols.

The TEA and $C_{2-14}$ olefins from unit 16 are cooled and conveyed via conduit 17 to ethylene flash separator 18. Ethylene vapor is removed and recycled to chain growth reactor 1. Bottoms from separator 18 are transferred via conduit 19 distillation unit 20 which distills mainly $C_{4-8}$ α-olefins overhead. Bottoms from unit 20 comprises mainly TEA and $C_{10-14}$ α-olefins and is recycled via conduit 4 wherein TEA forms part of the TEA feed and the $C_{10-14}$ α-olefins function as solvent in the chain growth reactor.

The various α-olefin streams taken overhead from units 9, 11 and 20 are fed to a product distillation section (not shown) wherein the various α-olefin cuts are separated for sales.

We claim:
1. A process for separating an aluminum alkyl chain growth product comprising $C_{12-14}$ α-olefins including 1-dodecene and 1-tetradecene and triethyl aluminum said process comprising:
    (A) feeding said chain growth product to an intermediate point of a rectification column, said rectification column being maintained under vacuum such that in operation the rectification section at said intermediate point is at a temperature in the range of 250°-260° F. and the overhead temperature is about 190°-240° F. whereby triethyl aluminum entering said rectification section is in the form of triethyl aluminum dimer thereby increasing its molecular weight and decreasing its volatility,
    (B) distilling at least 10 weight percent of said $C_{12-14}$ α-olefins in the feed mixture overhead from said rectification section and
    (C) removing over 50 weight percent of said triethyl aluminum in the feed mixture as a bottoms stream from said rectification column.
2. A process of claim 1 wherein said vacuum in said rectification section is in the range of 5-30 torr.
3. A process of claim 2 wherein said vacuum is in the range of 15-25 torr.
4. A process of claim 1 wherein said chain growth product fed to said rectification column comprises (a) 5-75 weight percent of a mixture of trialkyl aluminum compounds of which about 2-10 weight percent is triethyl aluminum and the remainder are higher trialkyl aluminum compounds and (b) 25-95 weight percent α-olefins of which about 5-90 weight percent are 1-tetradecene.
5. An aluminum alkyl chain growth process comprising:
    (A) feeding tri-lower alkyl aluminum and ethylene to a reaction zone maintained under chain growth conditions of about 200°-300° F. at 2000-3500 psig,
    (B) feeding chain growth product from step (A) to a flash separation zone wherein $C_{2-10}$ olefins are flashed from the chain growth product leaving a topped chain growth product comprising a mixture of $C_{12-20}$ α-olefins including 1-dodecene and 1-tetradecene and triethyl aluminum, and a poisson distribution mixture of tri-$C_{4-20}$ alkyl aluminums,
    (C) feeding said topped chain growth product to an intermediate point of a rectification column, said rectification column being maintained under vacuum such that in operation the rectification section at said intermediate point is at a temperature in the range of 250°-260° F. and the overhead temperature is about 190°-240° F. whereby triethylaluminum entering said rectification section is in the form of triethyl aluminum dimer thereby increasing its molecular weight and decreasing its volatility,
    (D) distilling at least 10 weight percent of said 1-dodecene and 1-tetradecene in the feed as overhead from said rectification section and
    (E) removing $C_{14-20}$ α-olefins, triethyl aluminum and a poisson distribution of tri-$C_{4-20}$ alkyl aluminums as a bottom stream from said rectification column.
6. A process of claim 5 wherein said vacuum is in the range of 15-25 torr.
7. A process of claim 5 wherein said bottoms stream and ethylene are fed to an ethylene displacement reaction zone to form a displacement product comprising triethyl aluminum ethylene, $C_{4-20}$ α-olefins, and minor amounts of higher alkyl aluminums.
8. An aluminum alkyl chain growth process comprising:
    (A) feeding ethylene, triethyl aluminum and a recycle stream comprising triethyl aluminum and $C_{10-14}$ α-olefins to an ethylene chain growth reactor, said ethylene, triethyl aluminum and recycle stream being in proportion such that the ethylene:triethyl aluminum mole ratio is about 4-10:1, to obtain a chain growth product,
    (B) flashing ethylene and $C_{4-10}$ α-olefins from said chain growth product to obtain a topped chain growth product comprising $C_{12-20}$ α-olefins including 1-dodecene and 1-tetradecene, triethyl aluminum and tri-$C_{4-20}$ alkyl aluminum,
    (C) feeding said topped chain growth product to an intermediate point in a rectification column, said rectification column being maintained such that the temperature at said intermediate point is about 250°-260° F. and the overhead temperature is about 190°-240° F. and under vacuum sufficient to cause at least 10 weight percent of said 1-dodecene and 1-tetradecene to distill overhead resulting in a bottoms stream comprising $C_{14-20}$ α-olefins, tri- ethyl aluminum and a mixture of tri-$C_{4-20}$ alkyl aluminums, (D) feeding said bottoms stream and ethylene to an ethylene displacement reactor to obtain a displacement product comprising ethylene, $C_{4-20}$ α-olefins, triethyl aluminum and minor amounts of higher alkyl aluminums, (E) separating ethylene from said displacement product, (F) distilling $C_{4-8}$ olefins from said displacement product to obtain a bottoms stream comprising triethyl aluminum and $C_{10-14}$ α-olefins and (G) recycling said bottoms stream from (F) to said chain growth reactor in step (A).

* * * * *